(12) United States Patent
Taheri

(10) Patent No.: US 6,478,818 B1
(45) Date of Patent: Nov. 12, 2002

(54) ARTERIAL BYPASS PROCEDURE

(76) Inventor: Syde A. Taheri, 268 Dan-Troy, Williamsville, NY (US) 14221

( * ) Notice: Subject to any disclaimer, the term of this patent is extended or adjusted under 35 U.S.C. 154(b) by 0 days.

(21) Appl. No.: 09/539,396

(22) Filed: Mar. 31, 2000

Related U.S. Application Data

(60) Provisional application No. 60/127,311, filed on Apr. 1, 1999, and provisional application No. 60/153,218, filed on Sep. 13, 1999.

(51) Int. Cl.$^7$ .................................................. A61F 2/06
(52) U.S. Cl. ....................................................... 623/1.36
(58) Field of Search ............................... 623/1.15, 1.36, 623/1.3; 604/8

(56) References Cited

U.S. PATENT DOCUMENTS

| | | | | |
|---|---|---|---|---|
| 4,164,046 A | * | 8/1979 | Cooley | 623/1.36 |
| 5,824,071 A | * | 10/1998 | Nelson et al. | 623/1.36 |
| 6,063,114 A | * | 5/2000 | Nash et al. | 623/1.36 |
| 6,074,416 A | * | 6/2000 | Berg et al. | 623/1.36 |
| 6,206,913 B1 | * | 3/2001 | Yencho et al. | 623/1.3 |
| 6,235,054 B1 | * | 5/2001 | Berg et al. | 623/1.36 |
| 6,258,120 B1 | * | 7/2001 | McKenzie et al. | 623/1.36 |

* cited by examiner

*Primary Examiner*—David H. Willse
*Assistant Examiner*—Suzette J. Jackson

(57) ABSTRACT

A support at the distal end of a bypass vein of either a synthetic material or of a saphenous vein for deployment inside an artery and the like to bypass a blockage in the artery, is described. The bypass vein is secured to a perimeter of the support with at least two protrusions extending from the support. The support and associate bypass vein are deployed inside the artery and then the support is pulled up against the artery wall by strings connected thereto to provide the bypass vein extending from the artery distal to the blockage. The other end of the bypass vein is then secured to artery proximate the occlusion to thereby establish blood flow.

16 Claims, 6 Drawing Sheets

ARTERIAL BYPASS PROCEDURE

CROSS-REFERENCE TO RELATED APPLICATION

This application is based on provisional applications Ser. Nos. 60/127,311, filed Apr. 1, 1999 and Ser. No. 60/153,218, filed Sep. 13, 1999.

BACKGROUND OF THE INVENTION

The present invention relates to a minimally invasive coronary bypass procedure which is the ideal operation for poor risk coronary artery patients. Existing techniques require either an extra-corporeal system or a time consuming anastomisis of the saphenosis vein to the coronary artery. In 1997, approximately 600,000 coronary artery bypasses were performed in the United States with a mortality rate of between 2% to 5%. While this mortality rate is relatively low, there is still room for improvement.

Accordingly, the present arterial procedure allows a surgeon to bypass an occluded coronary artery without an extra-corporeal system through a small chest incision and a graft insertion. The procedure provides a bypass vein, which is either a saphenous vein or of a synthetic material, having a first end sealingly secured to the occluded artery distal to the blockage by means of a novel barbed support. A second end of the bypass vein is secured to the occluded artery on the proximal side of the occlusion by means of a second one of the novel barbed support or by a stent to thereby establish unhindered blood flow.

SUMMARY OF THE INVENTION

The present arterial bypass procedure is performed under general anesthesia and routine preparation of the percutaneous approach. Through a limited left fifth intercostal space anteriorally, the chest is opened. Perocardium is incised and the coronary artery is identified. A needle is inserted into the designated coronary artery distal to the occlusion. This is followed by insertion of a guide wire and a peel-off sheath introducer. The bypass vein, mounted on a pusher device such as a coronary balloon, is then passed through the peel-off sheath. Under floroscopy guidance, the bypass vein is secured to the occluded artery distal to the occlusion while the peel-off sheath is removed. The opposite end of the bypass vein is then secured to the occluded vein proximal the occlusion, thereby bypassing the occlusion. The second end of the bypass vein is secured to the occluded vein by either a stent or a barbed support of the present invention.

These and other aspects of the present invention will become increasingly more apparent to those skilled in the art by reference to the following description and to the appended drawings.

DETAILED DESCRIPTION OF THE INVENTION

Figure 1:
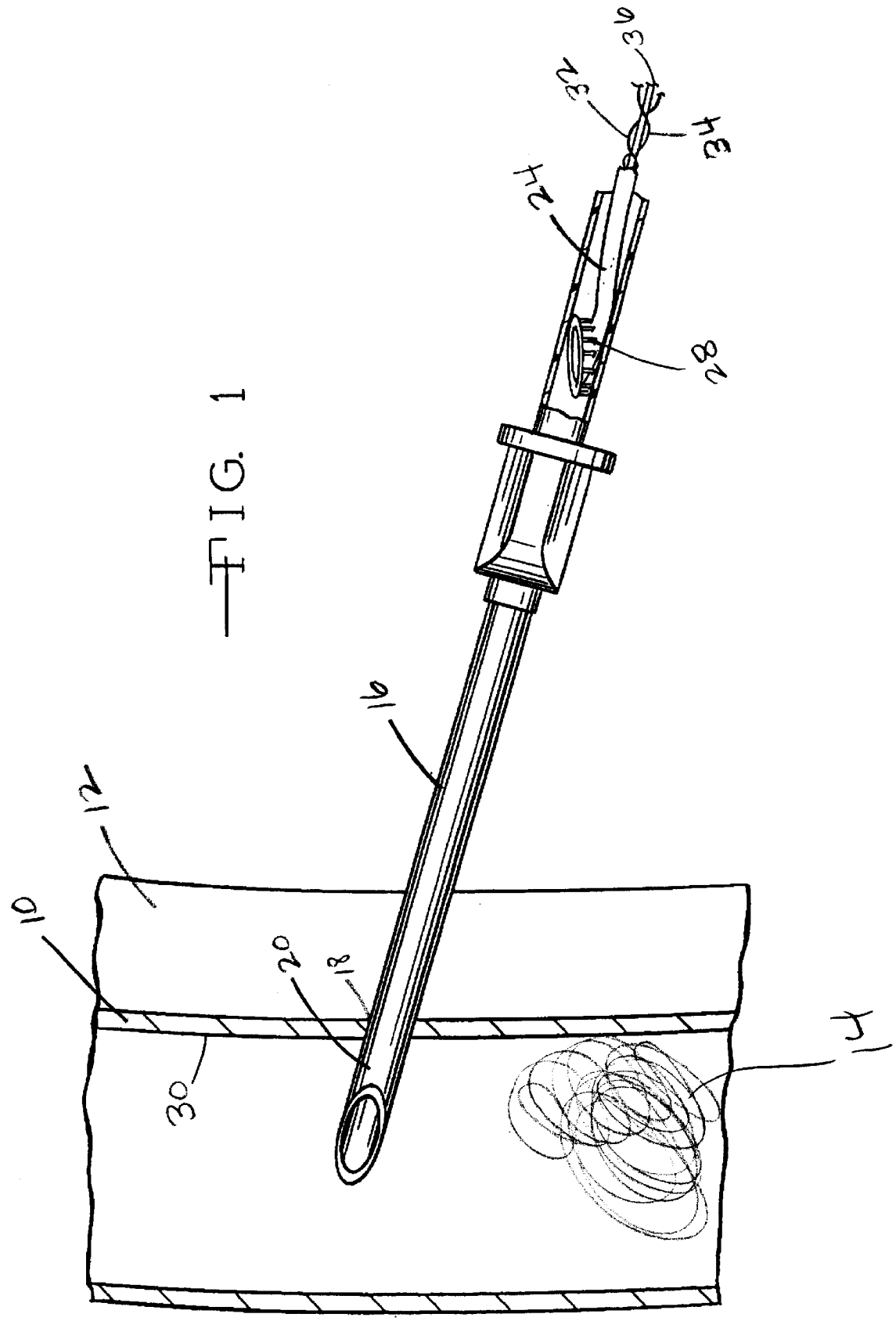
FIG. 1 is a perspective view of a support ring 22 and bypass vein 24 according to the present invention being moved through a sheath conduit 16 puncturing an occluded artery 10.

Referring now to the drawings, FIG. 1 shows an artery 10 proximate a muscle 12, such as a cardiac muscle and the like. An occlusion 14 blocks free and open blood flow through the artery 10.

According to the present invention, a sheath conduit 16 is moved through the muscle 12 and along a guide wire (not shown) previously positioned into the artery. The sheath conduit 16 extends through an opening 18 in the artery on one side of the occlusion 14 to position its distal end 20 inside the artery 10. The sheath conduit 16 is of a metallic material that is compatible with the physiology of the host body and is readily detectable by conventional imaging means. In that manner, the precise position of the sheath conduit 16 is determined by imaging its location until it is properly positioned in the artery 10.

The sheath conduit 16 serves as a lumen for placement of a ring support 22 (FIG. 4) and associated bypass vein 24 inside the artery 10. The support ring 22 is a self-expanding wire loop, such as a Nitinol wire, which provides an enclosing support. In a broader sense, however, the support can have a myriad of shapes including a coil spring shape (FIGS. 5 and 6) and a V-shape (FIG. 7). These alternate shapes will be described in detail hereinafter.

The ring 22 supports the bypass vein 24, which is a saphenous vein or of a synthetic, microporous material providing a lumen or conduit secured to the perimeter of the ring. In a preferred embodiment of the present invention, the support ring 22 is readily foldable into a shape that is movable through the sheath conduit, and the bypass vein 24 is of a polyurethane material sewn 26 or otherwise secured to the perimeter thereof.

In another embodiment of the present invention, the sheath conduit 16 serves to expand the opening 18 in the artery 10 to a size sufficient to have the sheath conduit 16 provided with a lumen that enables the support ring 22 to move there through in an unfolded condition. At such time as the sheath conduit 16 is removed from the artery 10, the opening 18 closes somewhat to a size that is smaller than the perimeter of the support ring 22. This is especially the case if the support ring 22 is moved through the sheath conduit 16 in an unfolded condition. If the support ring 22 is deployed in a folded condition and subsequently unfolded once it has left the sheath conduit 16, rebound of the artery tissue surrounding the opening is not as critical. In any event, the support ring 22 must be larger than the opening 18 in the artery 10 with the needle removed.

Figure 2:
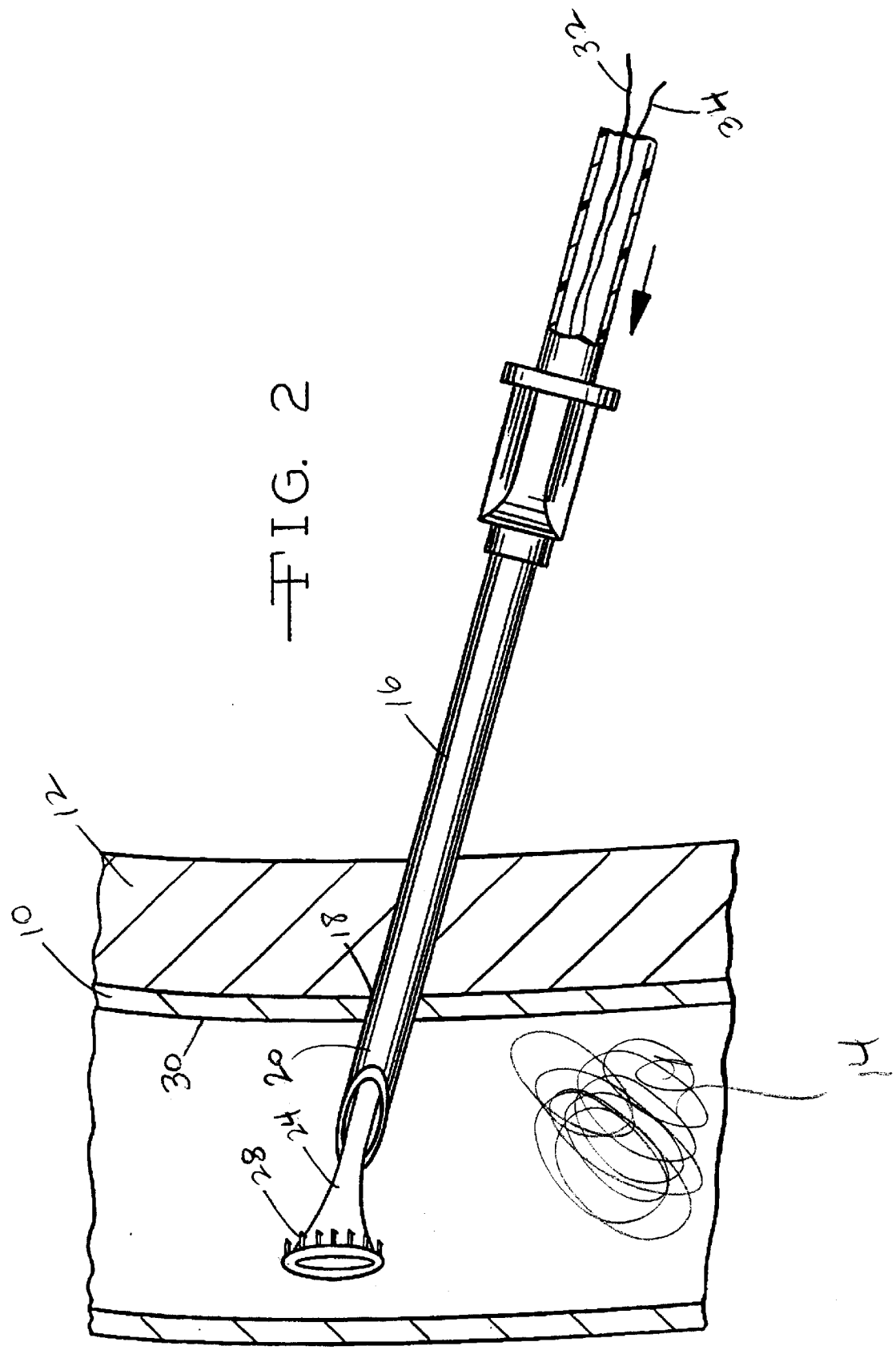
FIG. 2 is a perspective view of the support ring 22 and bypass vein 24 partially deployed out the distal open end 20 of the sheath conduit 16.

The support ring 22 is provided with a plurality of protrusions or barbs 28 spaced about the perimeter thereof. The barbs 28 are in the form of staples or wire-like projections. As shown in FIG. 2, just prior to closing the opening 18 in the artery 10 the barbs 28 point toward the inner side 30 of the artery. With this construction, the barbs 28 do not extend outwardly beyond the radial perimeter of the support ring 22, nor do they extend inwardly to interfere with an enclosed projection of the area bounded by the support ring 22.

The support ring 22 is further provided with a pair of spaced apart strings 32 and 34 connected to opposed portions of the ring. The strings are preferably of a degradable material that is safe to the host body. In an alternative embodiment, the strings are connected to spaced apart ones of the barbs 28. The string can extend through the conduit of the bypass vein or they can extend outside the bypass vein, and there can be more than two strings. For example, there could be four strings, one tied to each quadrant of the support ring. In a preferred embodiment of the present invention, the strings 32, 34 are coded, such as by color, to indicate the relative postion of the support ring 22 and its barbs 28 inside the artery 10 and, later, when the bypass vein 24 is secured to the artery. In still a further embodiment, there is only one string that bifurcates proximate the support ring 22 to connect to spaced apart portions of the support or to spaced apart barbs.

Figure 3:
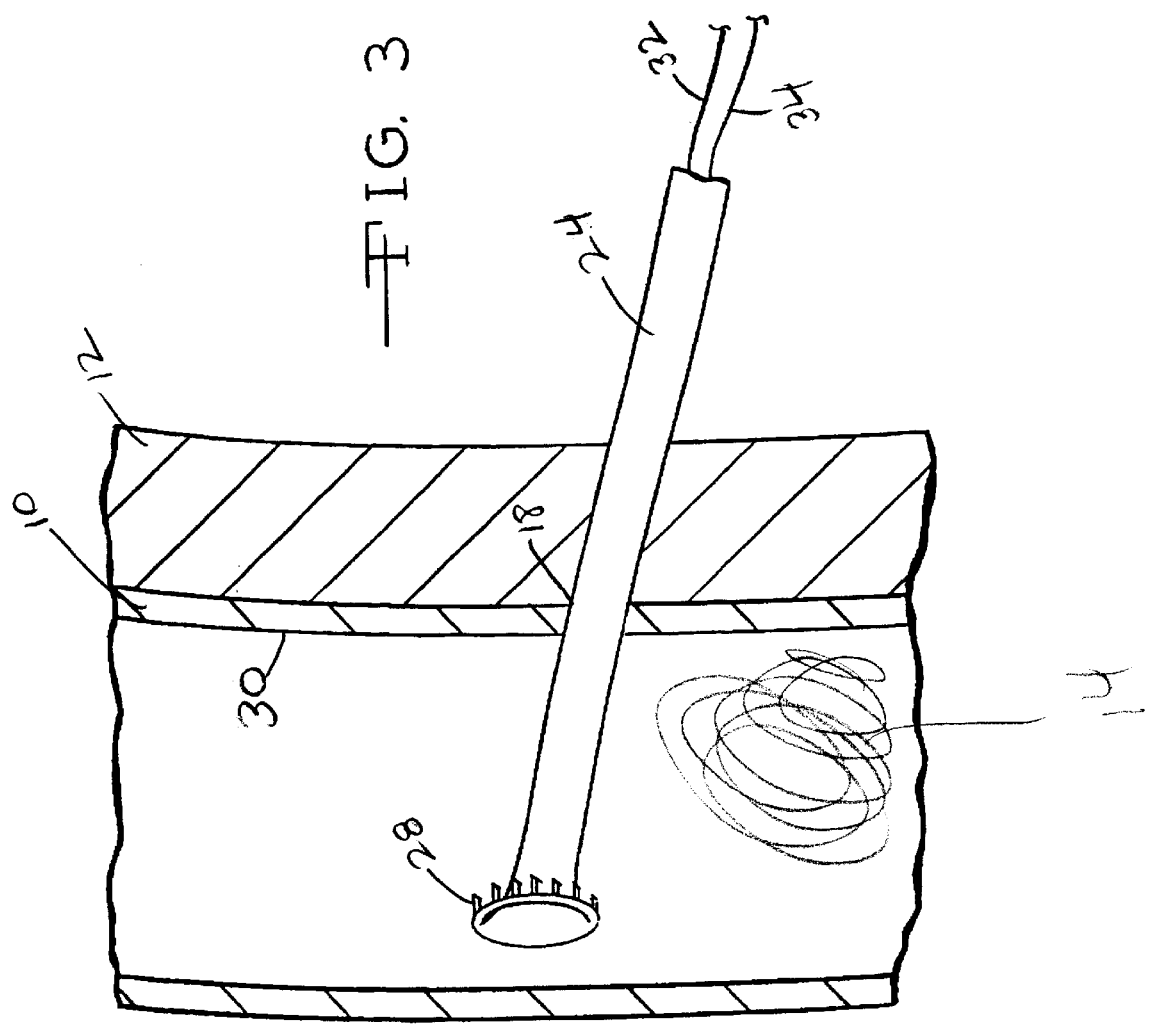
FIG. 3 is a perspective view of the support ring 22 and bypass vein 24 just before the support ring is moved into position to seal against the inside of the artery 10.
Figure 4:
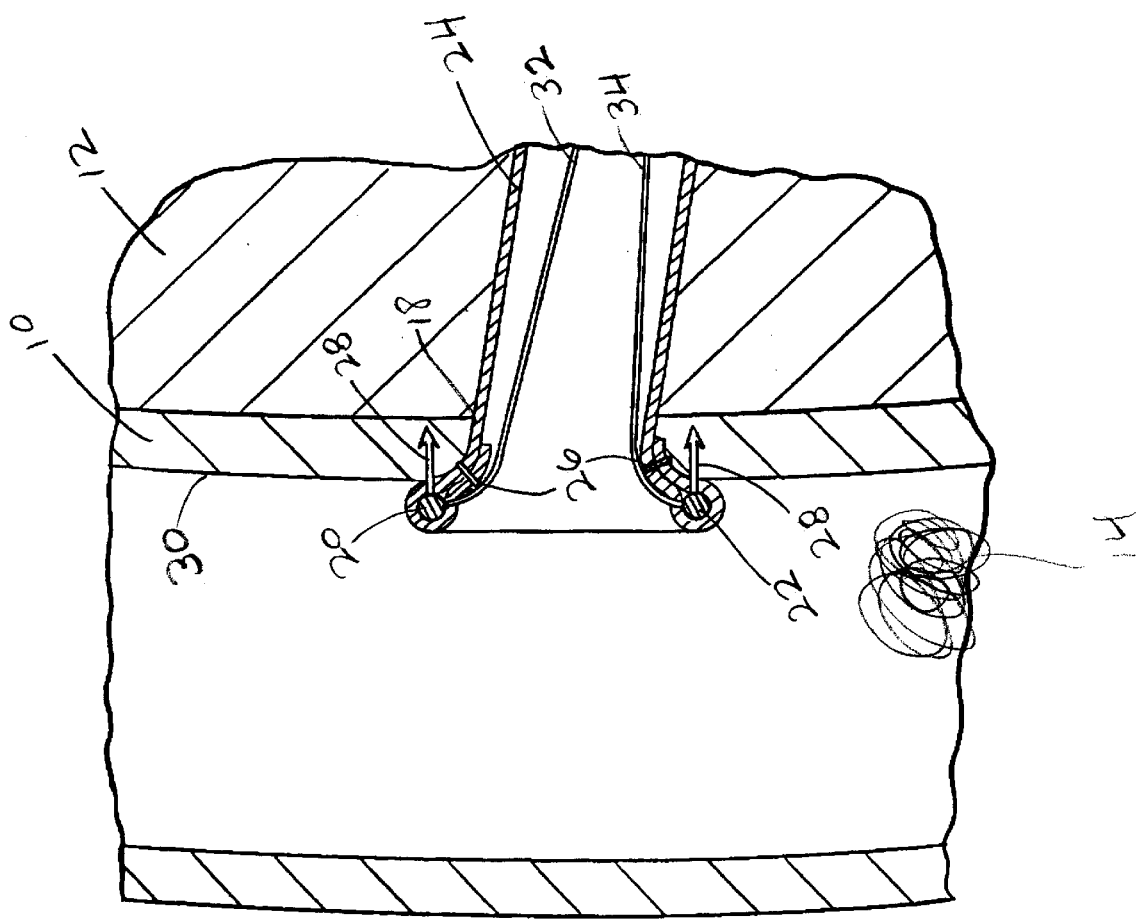
FIG. 4 is an enlarged, perspective view of the support ring 22 and bypass vein 24 secured to the occluded artery 10.

As shown in FIG. 1, to secure the bypass vein 24 to the artery, the support ring 22 connected to the strings 32, 34 is moved through the sheath conduit 16 and out a distal open end thereof by a push device 36. Accordingly, after the bypass vein 24 is deployed out the distal open end 20 of the sheath conduit 16 (FIG. 2), the conduit is removed from the artery 10 (FIG. 3) and the strings 32, 34 are pulled to move the bypass vein 24 including the support ring 22 up against the inner side 30 of the artery 10. The strings 32, 34 are further pulled to cause the barbs 28 to pierce the artery 10 surrounding the puncture with the barbs anchoring the support ring 22 in place. Accordingly, the support ring 22 is circular or oval and is of a size sufficient to surround the puncture. The support ring, being flexible, also readily conforms to the non-planar shape of the artery to effectively seal against the inner side 30 of the artery surrounding the opening 18 (FIG. 4).

While it is within the scope of the present invention to secure the strings 32, 34 to opposed portions of the support ring 22 or to diametrically opposed protrusions 26, it is most preferred to secure the strings to the support ring. That way, the strings do not interfere with movement of the protrusions through the arterial wall. After the bypass vein 24 is in place, the strings are then temporarily secured to the skin for future removal.

Finally, the proximal end (not shown) of the synthetic vein 24 is sutured or stented to a second opening (not shown) in the artery 10 proximal the occlusion 14. Once both ends of the bypass vein 24 are secured, circulation to the ischemic portion of the myocardium is established. The arterotomy incision is then closed.

Figure 5:
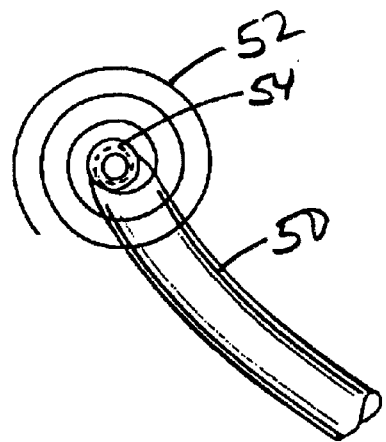
FIGS. 5 and 6 are perspective views of an alternate embodiment of the present invention including a bypass vein 50 secured to a coil spring 52.
Figure 6:
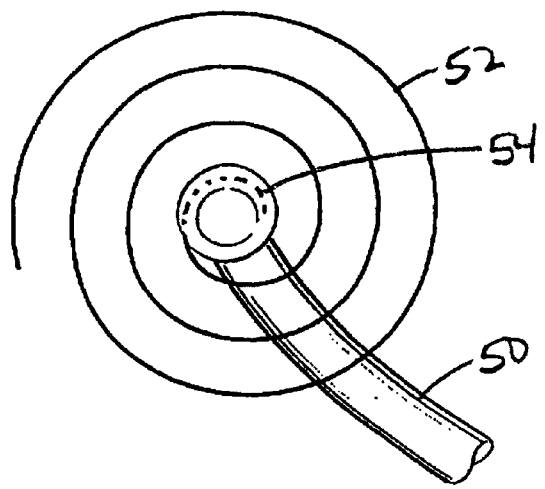
Figure 7:
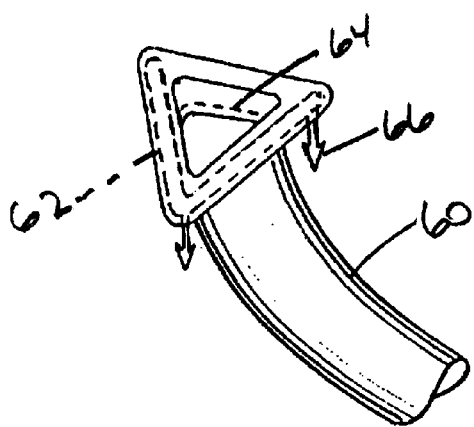
FIG. 7 is a perspective view of an alternate embodiment of the present invention including a bypass vein 60 secured to a V-shaped member 62.

An alternate embodiment of the present invention is shown in FIGS. 5 and 6. This embodiment comprises a bypass vein 50 secure to a coil spring 52. The bypass vein 50 is secured to the spring 52 at a central location by stitches 54 and the like, and the spring is deployed through the sheath conduit in a relatively tightly coiled condition (FIG. 5). Once the coil spring/bypass vein assembly is moved out through the distal open end of the sheath conduit, the spring uncoils (FIG. 6) to a size sufficient to seat against the artery side wall. While not shown, the coil spring is provided with barbs in a similar manner as the previously described support ring 22 to anchor the spring in the artery side wall.

Another embodiment of the present invention is shown in FIG. 7 comprising a bypass vein 60 secured to a V-shaped member 62 by stitches 64 and the like. The V-shaped member 62 is readily folded up to provide for moving it and the bypass vein 60 through the sheath conduit to deploy the assembly in the occluded artery. Once the V-shaped member has moved out the distal open end of the sheath conduit, the V-shaped member expands to its unfolded size and the barbs 66 are anchored to the artery side wall, as previously described, to connect the bypass vein 60 to the occluded artery.

Figure 8:
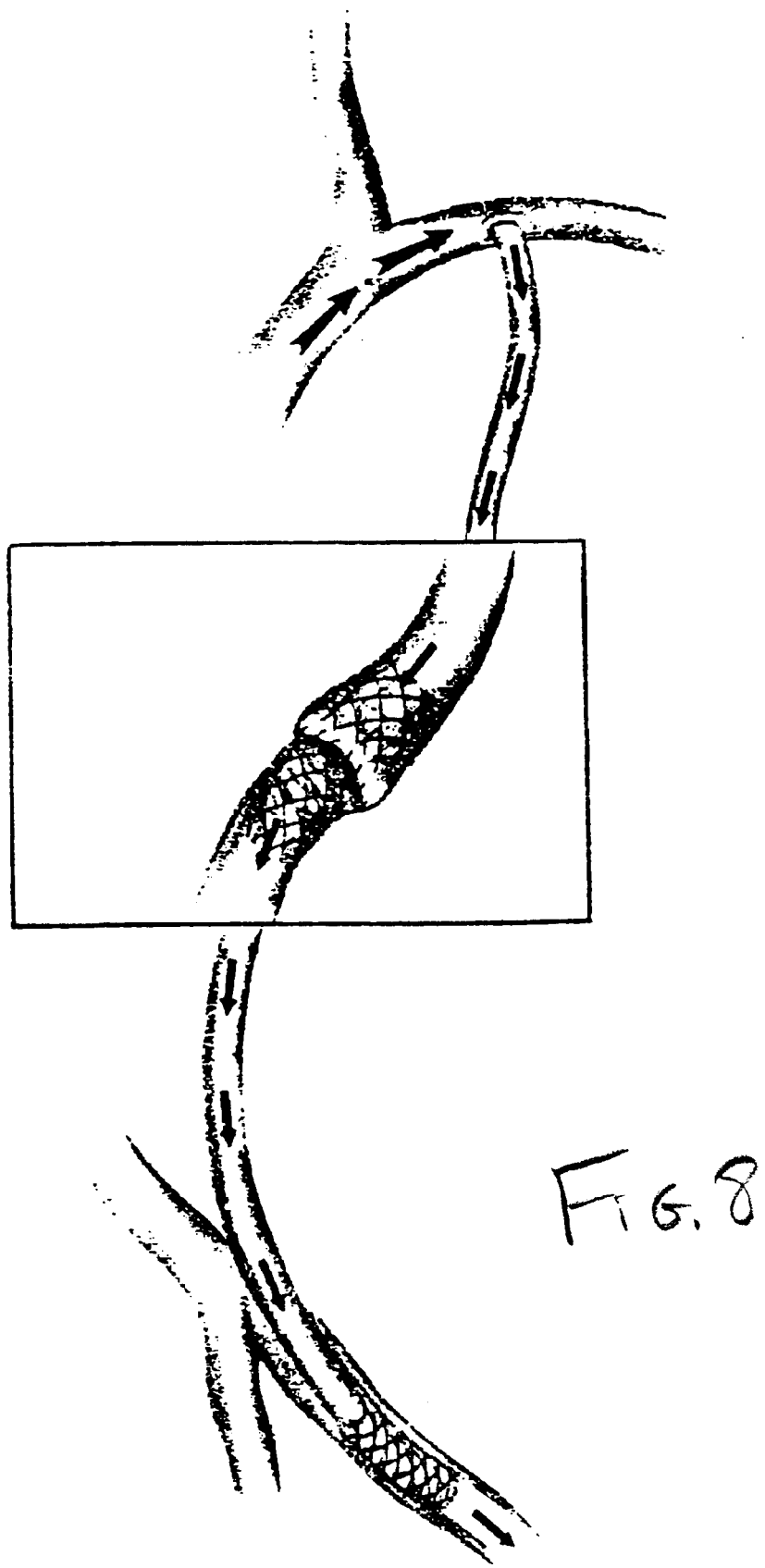
FIG. 8 is a perspective view showing two bypass veins according to the present invention use to bypass an occluded artery.

Also, it is contemplated by the scope of the present invention that there can be one of the present invention support structures at each end of the bypass vein to provide the arterial by-pass. In that case, there would actually be two bypass veins secured to the occluded artery on opposite sides of the occlusion 14 (FIG. 8). After the two bypass veins are deployed and secured to openings in the artery on the distal and proximal sides of the occlusion 14, their respective opposite ends are then sewn or secured together to complete the bypass procedure. In the alternative, there could be one bypass vein having the novel barbed ring support of the present invention at both of its ends. To secure the second barbed ring support, the strings are provided on the outside of the bypass vein so that they can be removed.

While the present invention has been described with respect to a coronary bypass procedure, it should not be so limited. Those skilled in the art will readily recognize that the present procedure can be used to short circuit or bypass any occluded artery, no matter where it exists, such as an occluded artery in the legs. Further, a surgical procedure with more than one vein bypass according to the present invention is contemplated.

It is appreciated that various modifications to the inventive concepts described herein may be apparent to those of ordinary skill in the art without departing from the spirit and scope of the present invention as defined by the herein appended claims.

What is claimed is:

1. A device for use in bypassing an occluded artery, which comprises:
   a) support structure configured for securement to a bypass lumen;
   b) at least two protrusions extending from spaced apart portions of the support structure, the protrusions comprising distal ends having barbs; and
   c) at least one string connected to either the support structure or to the protrusions.

2. The device of claim 1 wherein the support structure has a circular shape selected from the group consisting of a ring, a V-shape and a coil spring.

3. A device for use in bypassing an occluded artery, which comprises:
   a) an enclosing support having a bypass lumen secured to a perimeter thereof;
   b) at least two protrusions extending from spaced apart portions of the support, the protrusions comprising distal ends having barbs; and
   c) at least one string connected to either the support or to the protrusions.

4. The device of claim 3 wherein the enclosing support has a circular shape.

5. The device of claim 3 wherein the enclosing support is of a flexible material.

6. The device of claim 3 wherein the bypass lumen is of either a synthetic material or is a saphenous vein.

7. The device of claim 3 wherein the at least two strings are color coded.

8. A method for use in bypassing an occluded artery, comprising the steps of:
   a) providing a conduit extending through a side wall of the artery with a distal open end of the conduit positioned proximate an inner side of the artery;

b) providing a support having a bypass lumen secured to a perimeter thereof, wherein there are at least two protrusions extending from spaced apart portions of the support, the protrusions comprising distal ends having barbs that anchor the lumen to the body tissue;

c) providing at least one string connected to either the support or to the protrusions;

d) moving the support and bypass lumen along the conduit and out the distal open end thereof to position the support proximate the inner side of the artery with the protrusions extending toward the artery side wall;

e) moving the conduit so that its distal open end no longer resides proximate the inner side but, instead, resides proximate a near side of the artery; and f) pulling on the string to cause the support and bypass lumen to move against the inner side of the artery with the protrusions embedded in the artery side wall and the bypass lumen extending out the opening in the artery.

9. The method of claim 8 including securing an opposite end of the bypass lumen to the artery on an opposite side of the occlusion to establish blood flow.

10. The method of claim 8 including providing the enclosing support having a circular shape.

11. The method of claim 8 including providing the enclosing support of a flexible material that readily conforms to the shape of the inner side of the artery.

12. The method of claim 8 including providing the by pass lumen of either a synthetic material or of a saphenous vein.

13. The method of claim 8 including providing the enclosing support in a folded shape as it is moved through the conduit.

14. The method of claim 8 including providing the enclosing support in an unfolded, substantially planar shape as it is moved through the conduit.

15. The method of claim 8 including providing at least two strings connected to either the enclosing support or the protrusions.

16. The method of claim 8 including color coding the at least two strings.

* * * * *